United States Patent
Clinton

(10) Patent No.: US 6,170,335 B1
(45) Date of Patent: Jan. 9, 2001

(54) METHOD AND APPARATUS FOR MEASURING THE CHARACTERISTICS OF MEAT

(76) Inventor: Robert P. Clinton, 701 Carlisle Dr., Arnold, MD (US) 21012

( * ) Notice: Under 35 U.S.C. 154(b), the term of this patent shall be extended for 0 days.

(21) Appl. No.: 09/121,838

(22) Filed: Jul. 24, 1998

Related U.S. Application Data

(63) Continuation-in-part of application No. 08/900,356, filed on Jul. 25, 1997, now Pat. No. 5,872,314.

(51) Int. Cl.$^7$ ..................................................... G01N 29/00
(52) U.S. Cl. .................................................................. 73/629
(58) Field of Search ............................... 73/596, 627, 629

(56) References Cited

U.S. PATENT DOCUMENTS

| | | |
|---|---|---|
| 4,138,999 | 2/1979 | Eckhart et al. . |
| 4,359,055 | 11/1982 | Carlson . |
| 4,785,817 | 11/1988 | Stouffer . |
| 5,208,747 | 5/1993 | Wilson et al. . |
| 5,339,815 | 8/1994 | Liu et al. . |
| 5,353,796 | 10/1994 | Schroeder et al. . |
| 5,398,290 | 3/1995 | Bretbour . |
| 5,520,183 | 5/1996 | Lake et al. . |
| 5,573,002 | 11/1996 | Pratt . |
| 5,613,493 | 3/1997 | Schafer . |
| 5,617,846 | 4/1997 | Stouffer et al. . |
| 5,625,147 | 4/1997 | Miles et al. . |
| 5,641,907 | 6/1997 | Haagensen . |
| 5,673,647 | 10/1997 | Pratt . |
| 5,685,307 | 11/1997 | Holland et al. . |
| 5,717,142 | 2/1998 | Schafer . |

OTHER PUBLICATIONS

Bosoon Park et al.,*Determination of Beef Marbling Score Using Ultrasound A–Scan*, ASAE Technical Paper 90–6058 written for presentation at the 1990 International Summer Meeting of the American Society of Agricultural Engineers, Jun. 24–27, 1990.

Bosoon Park et al.,*Ultrasonic Frequency Analysis for Beef Quality Grading*, Paper No. 906573 written for presentation at the 1990 International Winter Meeting of the American Society of Agricultural Engineers, Dec. 18–21, 1990.

Keith A. Wear et al., Application of Autoregressive Spectral Analysis to Cepstral Estimation of Mean Scatterer Spacing, IEEE Transactions on Ultrasonics, Ferroelectrics, and Frequency Control, vol. 40, No. 1, Jan. 1993.

John R. Brethour,*Use of Ultrasonic Backfat Measures to Estimate Carcass Composition*, KAES Report of Progress No. 1784.

*Primary Examiner*—Richard A. Moller
(74) *Attorney, Agent, or Firm*—Dickstein Shapiro Morin & Oshinsky LLP

(57) ABSTRACT

A method and apparatus for measuring characteristics of meat, such as beef. More particularly, the invention uses quantitative analysis of ultrasonic A scan signals to measure the following characteristics of meat in real time: the percentage of intramuscular fat, the quality grade, the merit number, the depth of back fat, the depth of the rump fat, and the body composition (yield grade). The ultrasonic A scan signals are measured above the twelfth rib, above the thirteenth rib, between the twelfth and thirteenth ribs, and in the rump area. The invention can be used with either live or processed animals.

36 Claims, 14 Drawing Sheets

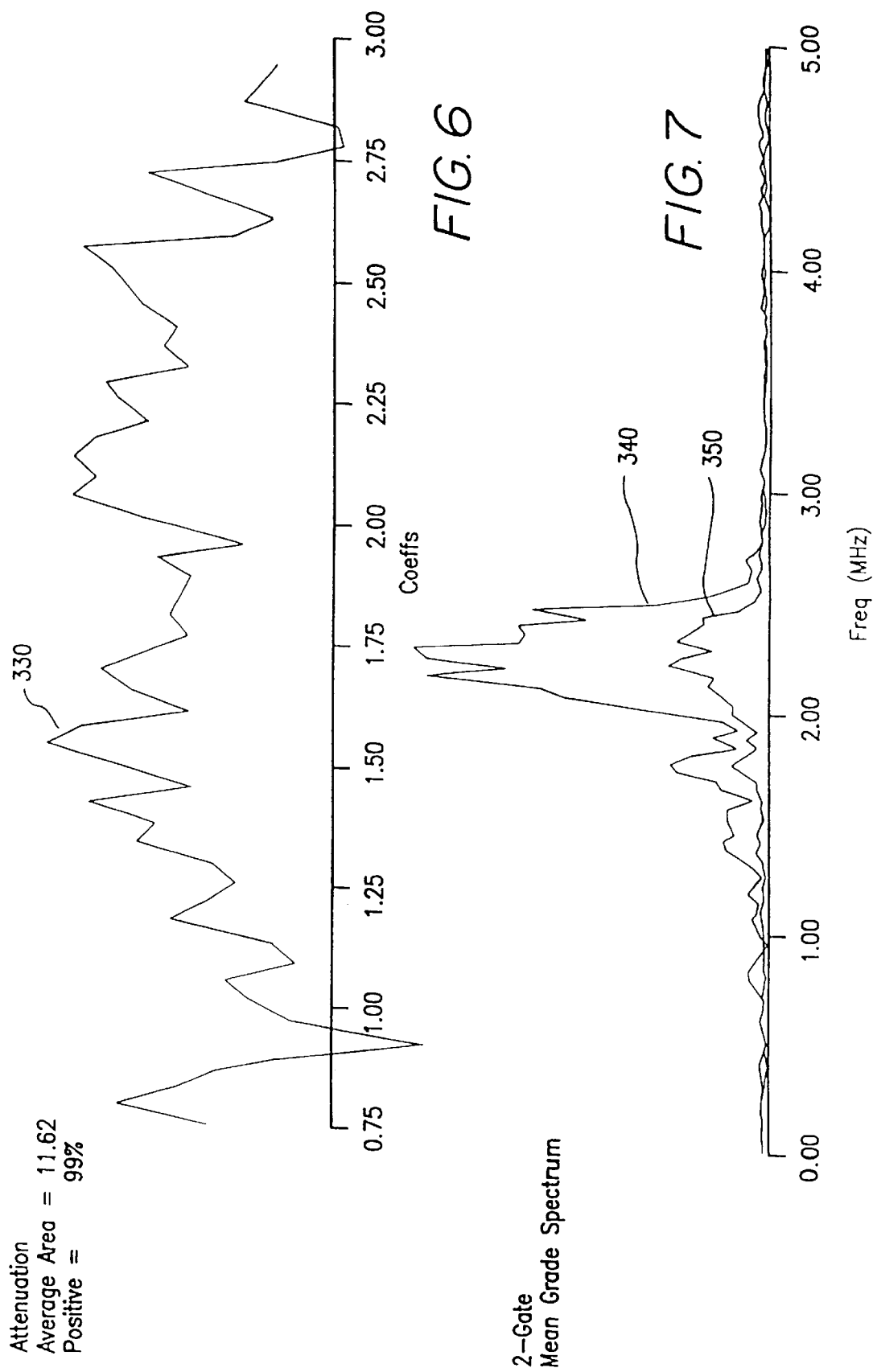

Individual Grade Spectrum

Mean Grade Spectrum

DMS INSTRUMENT DISPLAY
(BACKFAT)

DMS INSTRUMENT DISPLAY
(RUMPFAT)

METHOD AND APPARATUS FOR MEASURING THE CHARACTERISTICS OF MEAT

This application is a continuation-in-part of application Ser. No. 08/900,356, filed on Jul. 25, 1997, now U.S. Pat. No. 5,872,314, which is hereby incorporated by reference.

BACKGROUND OF THE INVENTION

1. Field of the Invention

The invention relates to a method and apparatus for measuring characteristics of meat, such as beef. More particularly, the invention uses quantitative analysis of an ultrasonic A scan signal to measure the following characteristics of meat: the percentage of intramuscular fat, the quality grade, the merit number, the depth of back fat, the depth of the rump fat, and body composition (also referred to as yield). Ultrasonic A scan signals are measured above the twelfth rib, above the thirteenth rib, between the twelfth and thirteenth ribs, and in the rump area of the animal (halfway between the hang bone and the pin bone). The invention can be used with either live or slaughtered animals.

2. Description of the Related Art

Traditionally, meat is visually inspected and graded after an animal has been slaughtered. With beef, for example, a cut is made between the 12th and 13th rib. A grader then visually inspects the exposed meat. Based on the appearance of this cross section, the grader classifies the meat according to predetermined standards that reflect the amount of intramuscular fat, or marbling, present in the meat. Typically, beef is classified according to U.S. Department of Agriculture (USDA) guidelines. Under USDA guidelines, meat can be classified as standard, select, choice or prime.

The visual inspection of meat has several disadvantages. First, the grading is subjectively based on the opinion of the grader. Different graders may assign different grades to the same piece of meat. Even the same grader might assign different grades to the same meat on different days. This is extremely important because the value of the meat is directly dependent on the grade it is assigned.

Visual grading of meat is also limited because the grader only has access to an area of the meat exposed at the cut. Generally, this grading is based solely on the quality of the meat at the cut between the 12th and 13th ribs. If that area does not accurately reflect the entire side of meat, the quality grade assigned to the meat will be incorrect.

Moreover, traditional techniques only provide information based on what is visually apparent to the grader. While the grader can visually estimate the marbling of the beef there is no way for him to determine the flavor and tenderness, or "merit," of the meat. This is important because one out of four sides of beef classified as "prime" is still rejected as unsatisfactory by discriminating customers, such as restaurants specializing in beef steak.

The traditional method obviously cannot be used to grade the quality of live cattle. Knowing exactly when to slaughter cattle is important to maximize profits. Ranchers send herds of cattle to feed lots prior to processing. The feed lots attempt to create the highest quality meat at the lowest cost. Currently, feed lots must estimate when an entire group, or pen, of cattle has been sufficiently fed. A pen might contain 50, 100, or even 150 head of cattle. If the cattle have not been fed long enough the quality of the meat, and its value, suffers. On the other hand, if the cattle are fed too long the increase in the quality of the meat will not justify the extra expense of feeding the animals plus a reduced grade penalty. Because there is no way to determine the quality of live cattle, an owner can only estimate the point of maximum profitability for a particular animal. For example, feed lot operators generally hold all pens a fixed number of days selected to maximize profits. Even with this approach, however, about one third of the individual animals in any given pen are under-fed and one third are over-fed. It would be desirable to know the quality of each animal in the pen so every animal can be processed at the peak of its profitability.

Because the traditional technique can only be used on slaughtered animals, it is of limited use when attempting to breed a more profitable herd. If the cattle owner had instant feedback about the quality of the animals in the herd, higher quality animals could be selected for breeding. This would improve the genetic quality of the herd over time. Currently, the cattle owner must wait until an animal has left the feed lot and been slaughtered before any decisions about the genetic quality of the animal can be made.

The lack of rapid feedback also prevents a cattle owner from responding to changes in consumer preferences. If consumers begin to demand leaner meat, for example, the cattle owner cannot make decisions about a herd until each animal has left the feed lot and has been slaughtered. This process can take up to six months or more.

To overcome some of these limitations, ultrasound technology has been used for the last two decades in animal research and applications. Ultrasound scanning technology utilizes high frequency sound waves to collect information from live tissue in a non-invasive manner. Efforts in the ultrasonic measurement of meat have concentrated on the use of real-time "B" mode imaging. B mode ultrasound, often used in medical applications, provides the operator with a two dimensional picture of the tissue being inspected. Brightness and texture are used in the image to characterize the animal's muscle tissue. By studying the two-dimensional image, the operator can characterize the muscle tissue and quality grade the animal. This approach, however, suffers from the same limitation as the traditional method because it is still based on the subjective opinion of the operator. Additionally, operators must be highly trained to interpret the B mode images correctly.

There have been attempts to mechanize and computerize the use of B mode imaging. Obtaining accurate measurements of these tissue characteristics is difficult because of speckle noise present in the image. Moreover, B mode imaging equipment is extremely expensive and transducers used with B mode imaging quickly wear out when used on rough surfaces, such as the hide of an animal. Equipment used with B mode imaging is also very large and does not lend itself to use in the field. Finally, B mode imaging is not able to determine the flavor and tenderness, or "merit," of the meat.

SUMMARY OF THE INVENTION

It is thus apparent from the above that there exists a significant need in the art for an improved method and apparatus for measuring characteristics of meat. Specifically, a more promising approach is disclosed to extract and identify features using the acoustic parameters of a back scattered ultrasound A scan signal. A quantitative analysis of the A scan signal provides definitive information about the characteristics of the meat.

It is therefore an object of this invention to provide a method and apparatus for measuring characteristics of meat using ultrasonic A scan signals.

It is another object of this invention to provide a method and apparatus for measuring the percentage of fat, the quality grade, the merit, the depth of back fat, the depth of the rump fat, and the body composition (yield).

It is another object of this invention to provide an inexpensive, real-time, durable and objective method and apparatus for measuring characteristics of meat.

It is another object of this invention to provide a method and apparatus for measuring characteristics of meat in both live and slaughtered animals.

It is another object of the invention to provide an apparatus for measuring the characteristics of meat in animals which is durable and small in size, preferably hand-held.

It is another object of the invention to provide a method and apparatus for measuring the characteristics of meat which gives the user an instantaneous indication of the quality of a live animal, so that feeding routines may be adjusted accordingly.

Briefly described, these and other objects of the invention are accomplished by providing a method of measuring characteristics of meat. An ultrasonic A scan transducer is positioned on the animal to be measured and an A scan signal is transmitted into the meat. The return signal is measured and used to calculate characteristics of the meat. Return signals are measured above the twelfth rib, above the thirteenth rib, between the twelfth and thirteenth ribs, and in the rump area of the animal (halfway between the pin bone and the hang bone).

The present invention also provides an apparatus for measuring characteristics of meat, including an A scan transducer that transmits an ultrasonic signal into the meat and receives a return signal. The transducer is connected to a first computer that calculates characteristics of the meat based on the return signal. This first computer may be a portable hand-held computer which processes the return signal. A second computer can be connected through a communication network to the first computer and used to analyze the return signals collected by the first computer. The first computer may also analyze the return signals, if desired.

These and other objects, advantages and features of the invention will be more readily understood by reference to the following detailed description of the invention, which is provided in connection with the several drawings attached herein.

BRIEF DESCRIPTION OF THE DRAWINGS

FIG. 6 shows the attenuation chart of the signature shown in FIG. 5.

FIG. 7 shows the dual gate mean grade power spectrum chart of the signature shown in FIG. 5.

DETAILED DESCRIPTION OF PREFERRED EMBODIMENTS

Figure 1:
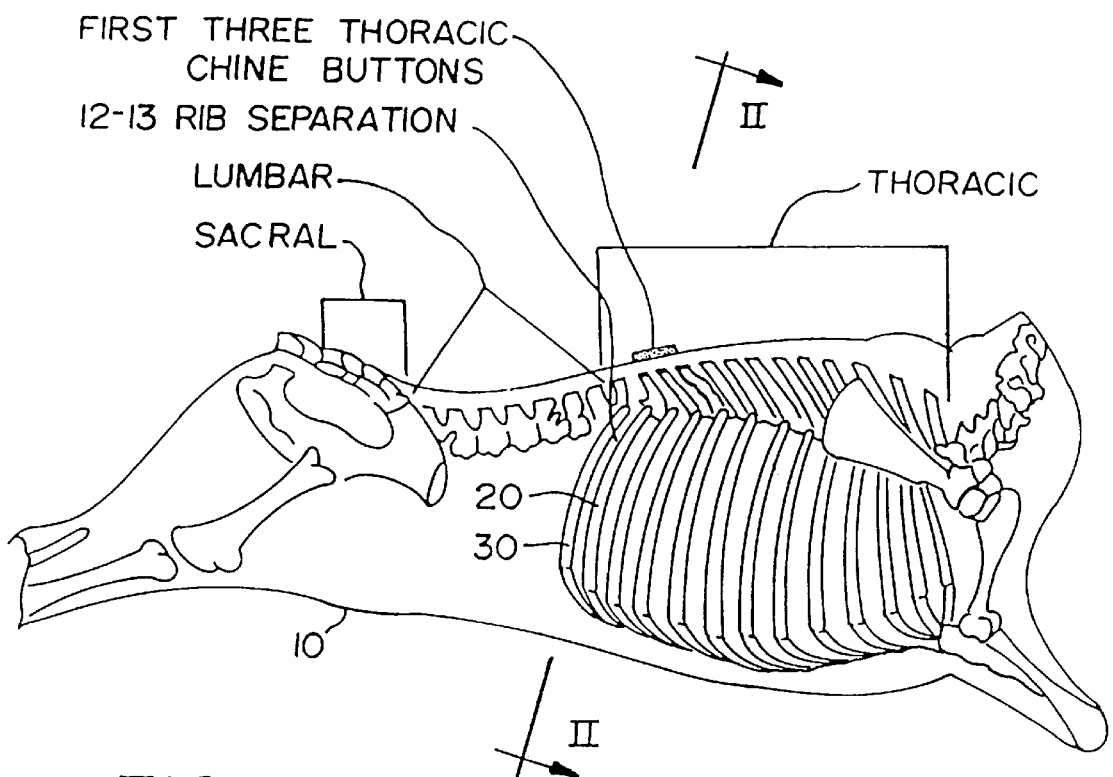
FIG. 1 shows a side skeletal view of a steer.

Referring now in detail to the drawings wherein like parts are designated by like reference numerals throughout, there is illustrated in FIG. 1 a side skeletal view of a beef animal 10. A grader generally has a cut between the twelfth rib 20 and the thirteenth rib 30 to grade the quality of the meat in the beef animal 10. In the embodiments of the present invention, ultrasonic A scan transducer signals are measured at the following four locations: (1) above the twelfth rib 20; (2) above the thirteenth rib 30; (3) between the twelfth rib 20 and the thirteenth rib 30; and (4) in the rump area (halfway between the hang bone and the pin bone). The phrase "above the rib" implies that the transducer is placed on the hide of the animal at the point closest to the rib at an angle as described below. The measuring position between the twelfth and thirteenth ribs is actually used to determine two different signals, so the total number of signals utilized by the present invention is five, as will be explained in detail below.

The user places an ultrasonic A scan transducer at the four locations described above to obtain five signals. The three signals taken at the positions around the twelfth and thirteenth ribs are used to determine the quality grade of the animal. A fourth signal taken in the rump area (halfway between the pin bone and the hang bone on the animal) is used to determine the rumpfat of the animal. A fifth signal is taken at the position between the twelfth and thirteenth ribs to determine the backfat of the animal. The rumpfat and backfat signals are used to calculate the body composition, or yield grade, of the animal using the following equations:

$$\text{percentage lean}=70.89-0.61*(\text{backfat})+0.0112*(\text{backfat})^2-0.284*(\text{rumpfat}),$$

where rumpfat and backfat are measured in mm.

$$\text{percentage fat}=13.10+0.86*(\text{backfat})-0.0157*(\text{backfat})^2+0.307*(\text{rumpfat}),$$

where rumpfat and backfat are measured in mm.

These equations were disclosed in a study entitled "Use of Ultrasonic Backfat Measures to Estimate Carcass Composition" by John Brethour, KAES Report of Progress No. 784, April 1997, p.10–11, which is incorporated herein by reference. Body composition or yield is determined by the percentage fat and percentage lean of the animal. By calculating the percentage fat and percentage lean, a USDA yield grade can be determined.

Figure 2:
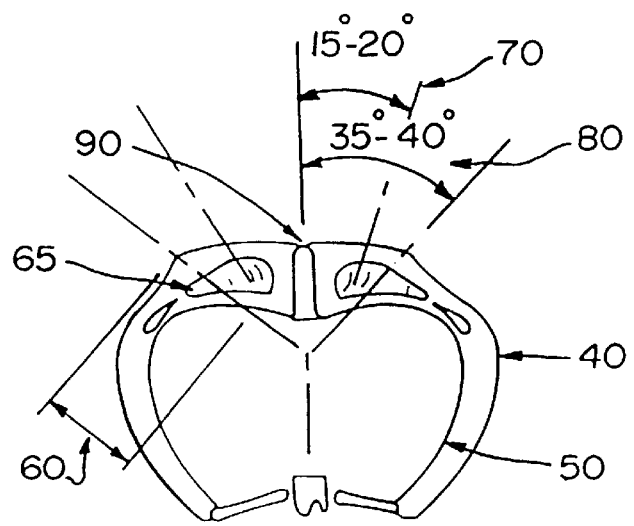
FIG. 2 is a cross sectional view taken along section line II—II of FIG. 1.

FIG. 2 is a cross sectional view taken along section line II—II of FIG. 1. The chine bone 90 is located at the top of the exposed rib 50. The grain of meat generally runs at an angle 70, which is between about 15° and about 20°. It has been determined that a transducer provides an accurate signal when offset from the grain by about 20°. Thus, the transducer should be placed on the hide 40 at an angle 80 of about 35° to about 40°. Vegetable oil should be spread on the hide allowing the transducer to make better contact with the animal. Also shown in FIG. 2 is a rib-eye steak area 65 with a given width 60 along the line perpendicular to the angle 80 at which a transducer should be positioned.

Figure 3:
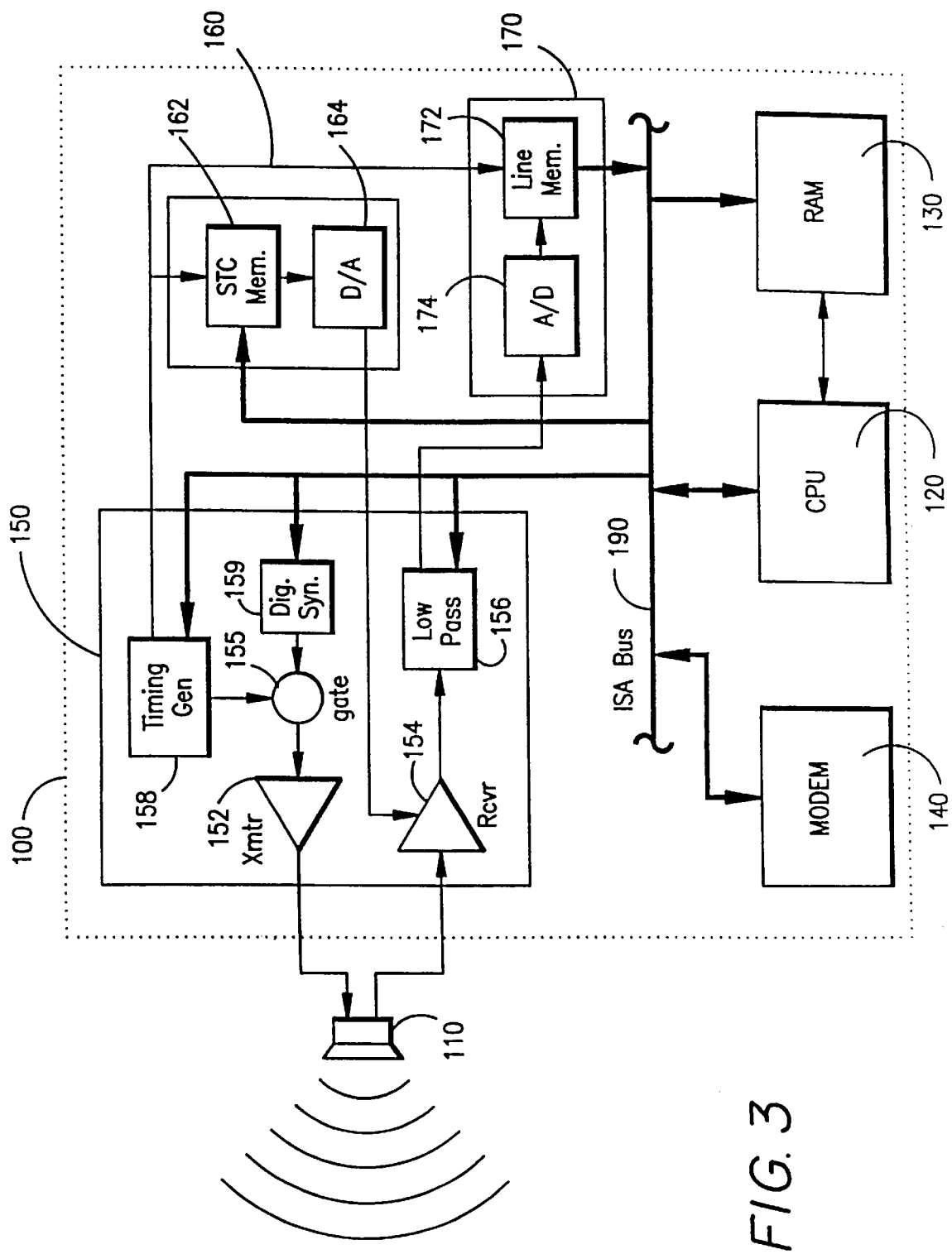
FIG. 3 shows a measuring apparatus according to a first embodiment of the present invention.

FIG. 3 shows a measuring apparatus according to a first embodiment of the present invention. A transducer probe 110 is connected to an IBM compatible computer 100 with a coaxial cable. The computer contains a CPU 120, such as a 486DX or PENTIUM processor, connected to system random access memory (RAM) 130 through a local computer bus. Both the CPU 120 and system RAM 130 are also connected to the computer's 16 data bit industry standard architecture (ISA) bus 190. A modem 140 can also be connected to the ISA bus 190. The modem 140 can be used to transmit data through a communication network to another computer (not shown) that will analyze the data.

The transducer probe 110 is a protected face longitudinal transducer and can have a frequency of 2.25 MHz and a nominal element size of 13 mm. Such a transducer probe is the Panameterics V606-RB. A 38 mm delay line can be used with this probe to improve near surface resolution.

The transducer probe 110 communicates with the computer 100 via an ultrasonic transceiver 150. The ultrasonic transceiver 150 has a digital synthesizer 159 connected to the ISA bus 190. The digital synthesizer 159 generates a wave form which passes through gate 155 to the transmitter amplifier 152. A timing generator 158 connected to the ISA bus 190 controls the gate 155. The amplified signal is sent to the transducer probe 110 and transmitted as an ultrasonic A Scan signal into a section of tissue (not shown). The Matec Instruments TB-1000 gated amplifier Toneburst plug-in card can be used for the ultrasonic transceiver 150.

The returning ultrasonic A Scan signal is received by the transducer probe 110 and input to a receiver amplifier 154. The amplified received signal is then sent to low pass filter 156, which is connected through an analog to digital converter 174 and line memory 172, as discussed below, to ISA bus 190.

The computer 110 also has a system board 160 with a sensitivity time control (STC) memory 162, such as an Intel 27128 EPROM, controlled by the timing generator 158. The STC memory 162 is connected to the ISA bus 190 and has an 8 bit connection to the digital-to-analog converter 164, such as a DAC 0800. Sensitivity gain control curves are stored in STC memory 162 and allow the digital-to-analog converter 164 to control the gain of the receiver amplifier 154.

Finally, the computer has a digital scope 170 with an analog-to-digital converter 174. The analog-to-digital converter has an 8 bit connection to a line memory 172. The line memory 172 is controlled by the timing generator 158 and is connected to the ISA bus 190. The analog-to-digital converter 174 receives the signal output by the low pass filter 156 in the ultrasonic transceiver 150, digitizes it and stores the results in the line memory 172.

The computer 100 can also have standard components, such as a keyboard, mouse, display terminal, operating system and printer, none of which is shown in FIG. 3.

Figure 13:
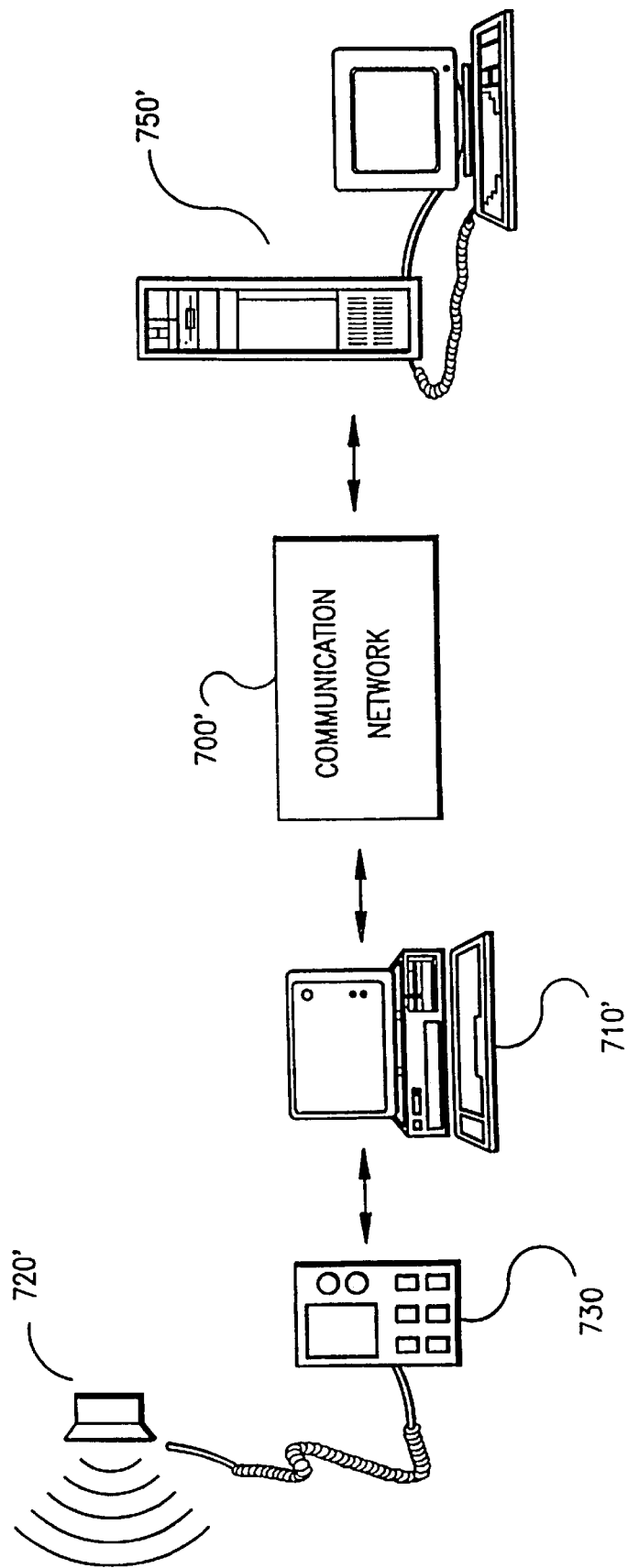
FIG. 13 shows the components of a measuring system according to a second embodiment of the present invention.
Figure 17:
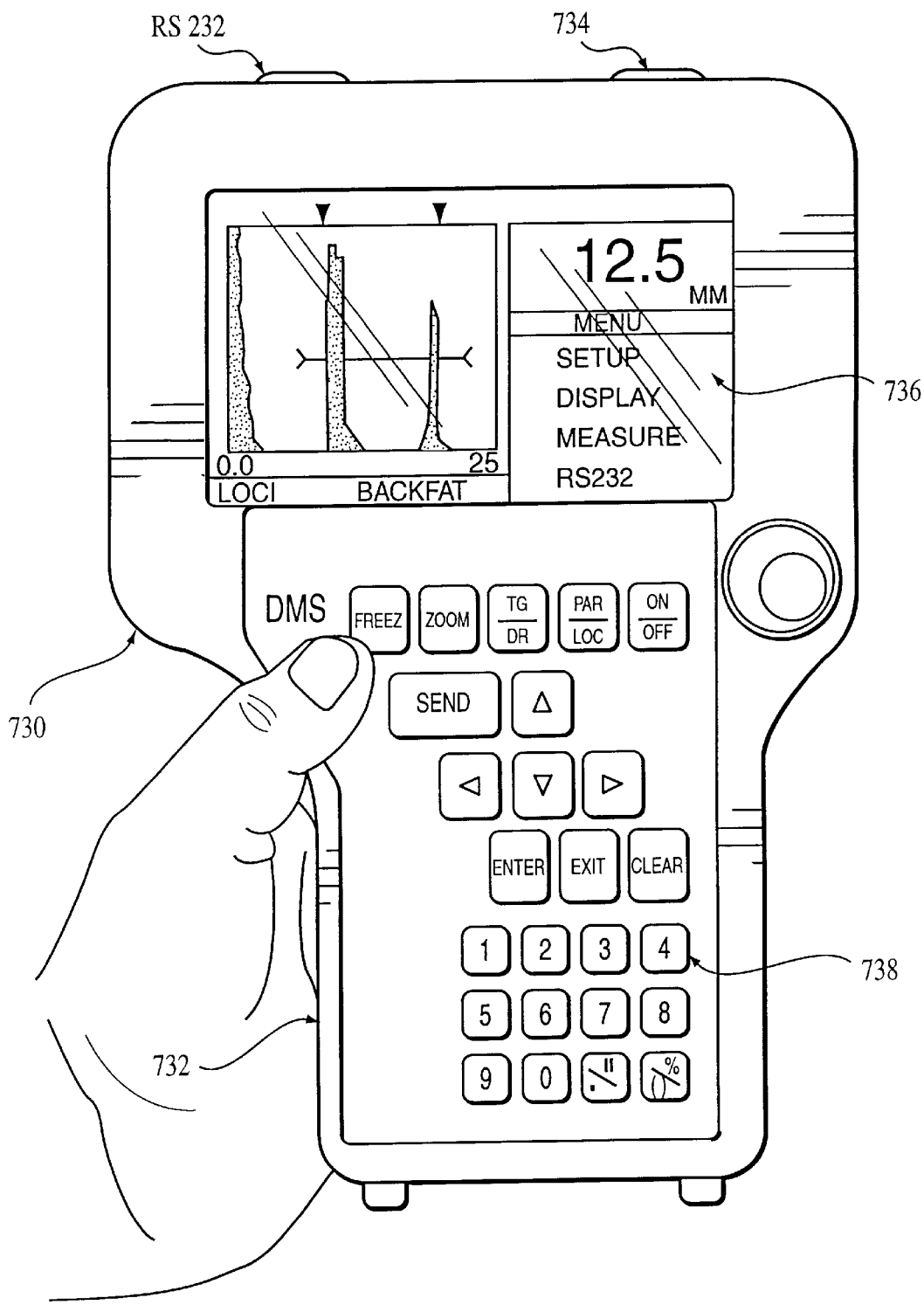
FIG. 17 shows a portable scanning unit of a second embodiment of the present invention.

In a second embodiment shown in FIGS. 13 and 17, a portable computer unit 730 is used to gather data. As shown in FIG. 13, this portable unit 730 communicates with a client PC 710' which, in turn, communicates with a server PC 750'. As can be seen in FIG. 17, the portable computer unit 730 is grippable by a handle 732 when in use. The portable unit 730 also includes a port 734 for attaching the transducer 110. The portable unit includes within it substantially the same elements included in the PC embodiment described above with reference to FIG. 3. The portable unit 730 will include a transceiver (not shown) for sending signals to and receiving signals from a remote computer. It may also incorporate a modem for sending signals to and receiving signals from the remote computer. The portable unit 730 also includes a display screen 736 and a keypad 738. A unit such as the Krautkramer Branson DMS, programmed with specialized measuring software, may be used for this portable unit. The portable unit can be used to measure the five return signals discussed above, namely, the three signals around the twelfth and thirteenth rib area, the backfat signal (measured between the twelfth and thirteenth ribs), and the rumpfat signal (measured in the rump area), for a multitude of animals. Then, when all animals have been measured and the return signals stored in the portable unit they can be downloaded to a PC (710' in FIG. 13) at a different location, either through a hard wire connection, through electromagnetic signal transmission, or by way of a modem connection. The PC 710' is in turn connected to a network controlled by server computer 750'. Alternately, the portable unit 730 can be loaded with software which would allow it to perform the calculations performed at the PC 710' and the server 750', thereby eliminating the need for such computers. The portable unit is advantageous because it is durable, gives the measurer more freedom, and does not require the PC to be located where the animals are worked and/or kept, which is often not the best environment for electronic equipment.

Figure 4:
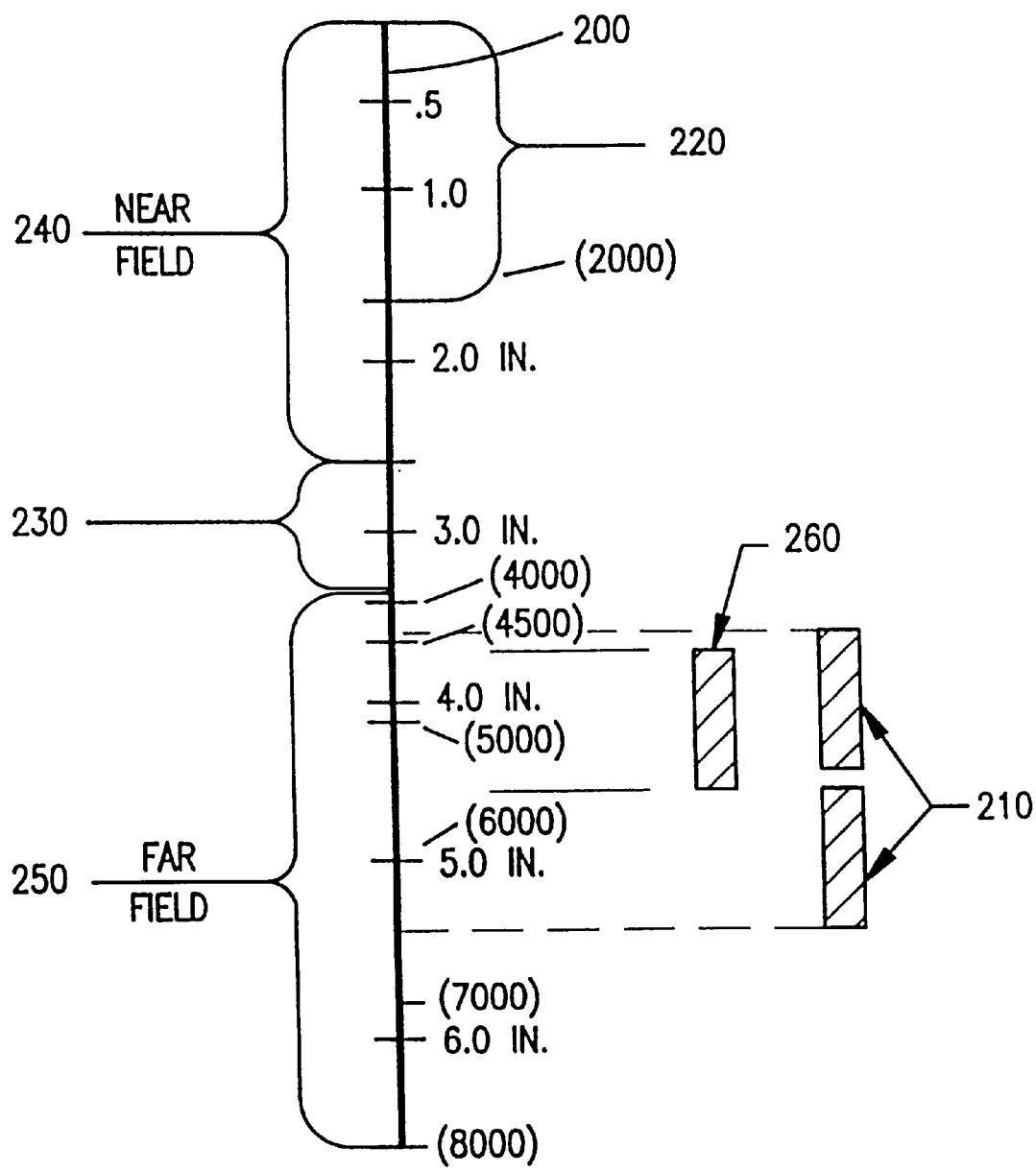
FIG. 4 shows the areas of transducer signal return according to depth.

FIG. 4 shows the areas of ultrasonic A scan signal received by transducer 110 according to penetration depth 200. Depth is shown both in terms of distance, labeled in inches, and the number of samples, shown in parenthesis. A 70 dB receiver can be expected to produce returns of approximately 8000 sample, or data, points. Using a 40 MHz sampling rate and assuming the speed of sound in tissue to be about 1540 m/sec, the entire 8000 data samples represents approximately 16 cm.

The sound field of the ultrasonic transducer contains two separate zones: the near field 240 and the far field 250. The near field 240 is the region directly in front of the transducer where the echo amplitude goes through a series of maxima and minima. The near field 240 (shown at the top of FIG. 4) can contain saturated return signals and is not used to determine the grade or merit of the meat. However, these saturated return signals can be used to determine the depth of back fat. The backfat depth 220 in the near field 240 can be up to 1.5 inches. The back fat area 220 of the return signal contains at least 2000 data points.

The far field 250 is the area beyond the near field 240 past the point 230 where the signal decays to zero pressure. The far field 250 is the area where the best signal returns are achieved. In the present invention, the far field corresponds to the area from about three to about six inches below the hide. This is the area of interest when determining the quality of the meat. A grade sample gate 260, used for grade and merit determinations, is located in the far field 250. The grade sample gate 260 contains at least 1000 data points. Two attenuation sample gates 210, used for attenuation determination, are also located in the far field 250. Each attenuation sample gate 210 contains at least 1000 data points.

Figure 5:
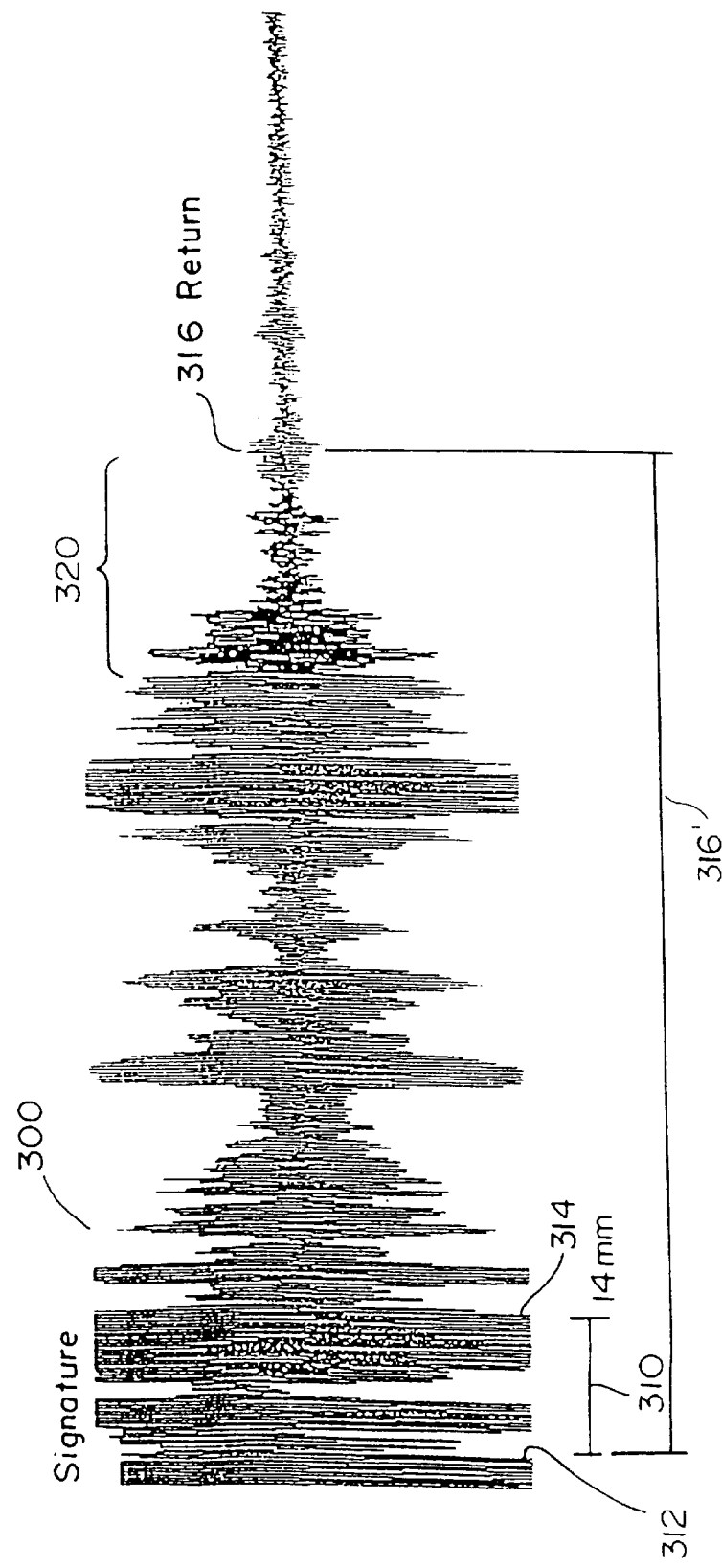
FIG. 5 shows a sample A scan transducer signature.

The first step in the quantitative analysis is to convert the ultrasonic return signal data into a digital signature. FIG. 5 shows a sample A scan transducer signature 300 obtained with the either the first or second embodiment of the present invention. The signature 320 in the far field is used to determine the quality grade and merit of the animal. The signature 310 in the near field is used to determine the depth of back fat. Thus, when measuring at the location between the twelfth and thirteenth ribs, the near field is concentrated on when measuring the backfat and rumpfat, and the far field is concentrated on when determining the quality grade.

Initially, five signatures are obtained by placing the transducer in the locations described above: above the twelfth rib; above the thirteenth rib; between the twelfth and thirteenth ribs; and in the rump area. As discussed above, the area between the twelfth and thirteenth ribs is used to measure two different signals, so the four locations actually produce 5 different return signals.

Figure 11:
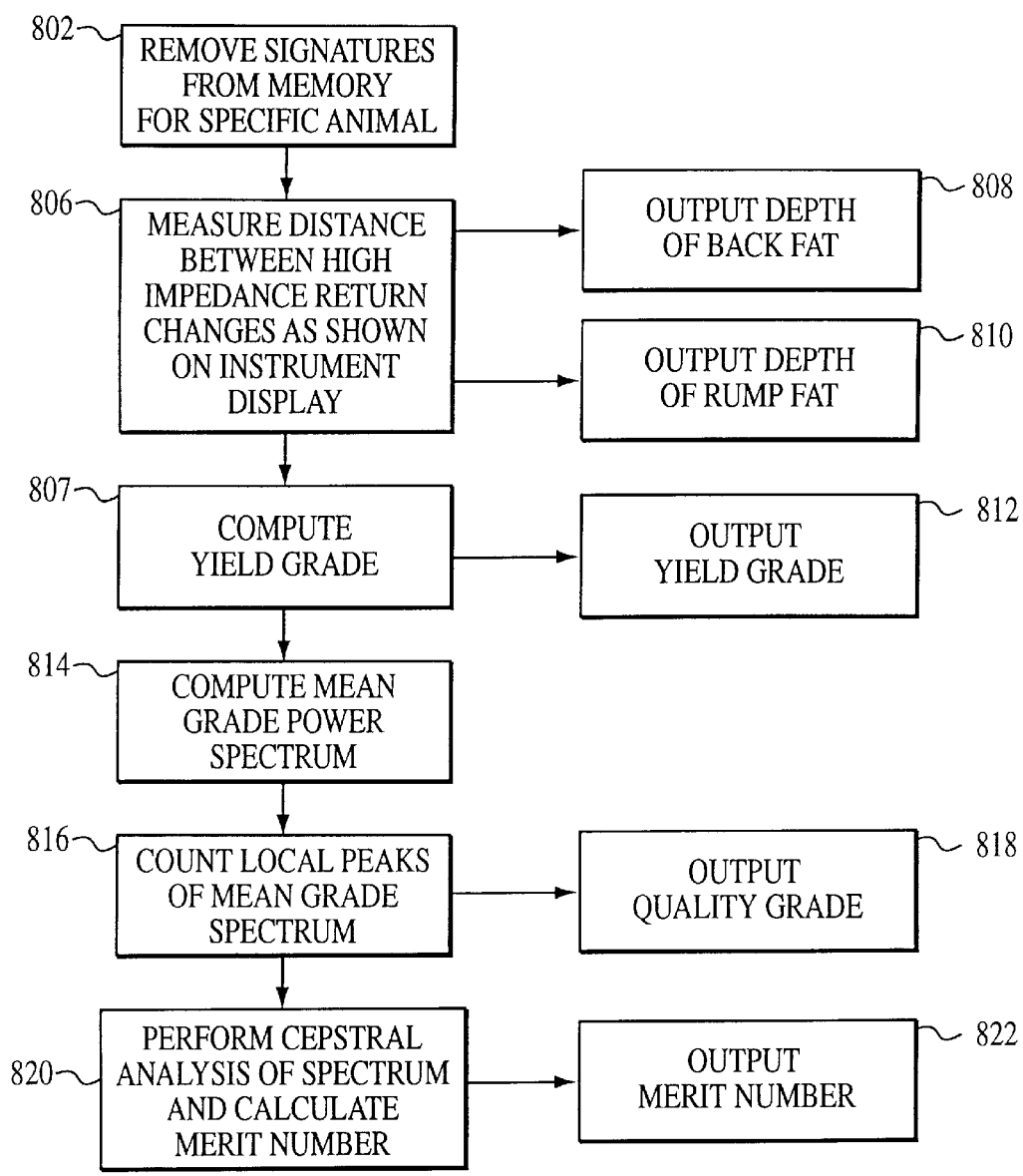
FIG. 11 shows a flow diagram of the steps performed to obtain the different characteristics of the meat specimen.

Each of the five signatures look substantially similar to the signature 300 shown in FIG. 5. The first three signatures are combined and used to determine the quality grade of the animal as described below with reference to FIG. 8. When determining this grade, the far field 320 of each signature 300 is concentrated on. When analyzing the fourth (rumpfat) and fifth (backfat) signals, however, the near field is concentrated on. As explained above, the fourth and fifth signals are used to determine the yield of the meat specimen. Each signature in the near field is examined to determine the points at which the signature decays from a high return to a low return. These signals represent changes in tissue type at that depth. The distance 310 between the first such reduction 312 and the third reduction 314 is the approximate depth of the back fat or rumpfat. The process of calculating and obtaining the backfat, rumpfat and yield grade is shown in FIG. 11 as steps 802, 806, 807, 808, 810 and 812. The process for determining quality grade and merit is shown in FIG. 11 as steps 814, 816, 818, 820 and 822.

Also shown in FIG. 5 is the grade sample gate area 320 of the signature 300. The grade sample gate area 320 is used for quality grade and merit determinations as described with respect to FIGS. 8 through 10.

FIG. 6 shows the attenuation 330 of the signature shown in FIG. 5. The attenuation 330 and 2-gate mean grade power spectrum charts 340, 350 (shown in FIG. 7) are generated by the computer based on the data from the two attenuation sample gates 210 shown in FIG. 4. These charts provide an indication of the quality of the return signal. The attenuation chart shows the amount of signal return loss between the first and second attenuation sample gates 210. The attenuation 330 shown in FIG. 6 is 99% positive, which represents a very reliable return signal. It has been found that the attenuation occurring parallel to the grain of a meat sample is approximately one-half as large as the attenuation occurring perpendicular to the grain of the meat sample. Thus, if the transducer is placed on the animal at an incorrect angle, the attenuation 330 might be only 50% positive. This would indicate that the return signal was not very reliable. Similarly, a low attenuation score might indicate that the contact between the transducer and hide was poor, and more vegetable oil should have been applied.

The mean grade power spectrum charts 340, 350 shown in FIG. 7 are also calculated using the two attenuation sample gates 210 and should display similar maxima and minima to indicate a reliable return signal. The mean grade power spectrums 340, 350 are calculated in a manner similar to that described with respect to FIG. 8 below.

Figure 8:
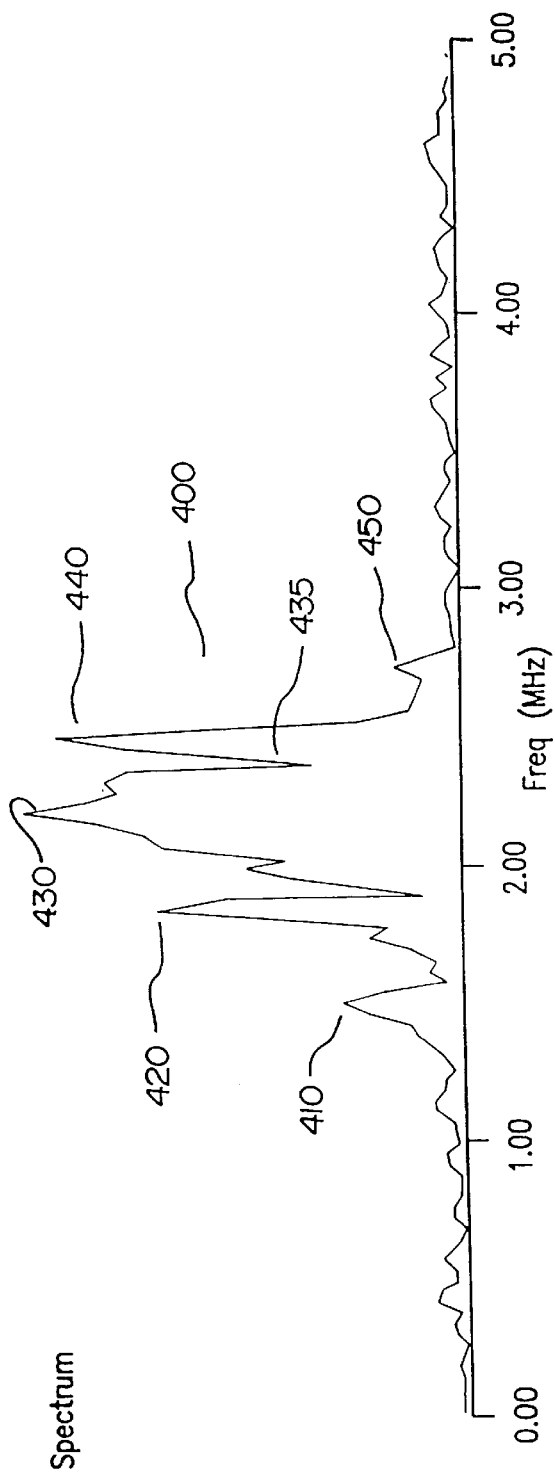
FIG. 8 shows an individual grade power spectrum of the signature shown in FIG. 5.

FIG. 8 shows an individual quality grade power spectrum 400 of the signature 300 shown in FIG. 5 using the quality grade sample gate area 320. Generating the individual grade power spectrum is performed by converting the digitized return signal into the frequency domain by means of a fast fourier transform (FFT). FFT is a mathematical algorithm used to calculate the frequency domain, or fourier transform of a time domain signal. The FFT equation is as follows:

$$X(m) = \sum_{n0}^{N-1} x_H(n) W^{mn}$$

In other words, the FFT transforms a time domain signal into the frequency domain. The power, or grade, spectrum 400 is a quantitative measure of this signal return.

It should be noted that the "score" traditionally assigned to meat samples is roughly equivalent to the percentage of intramuscular fat the meat contains. The USDA scores, and the related USDA quality grades, are given in Table 1.

TABLE 1

Meat scores and USDA quality grades.

| Score (% fat) | USDA Quality Grade (Marbling) |
| --- | --- |
| 2.00–2.99 | Standard (Traces) |
| 3.00–3.99 | Select (Slight) |
| 4.00–4.99 | Low Choice (Small) |
| 5.00–5.99 | Average Choice (Modest) |
| 6.00–6.99 | High Choice (Moderate) |
| 7.00–7.99 | Low Prime (Slightly Abundant) |
| 8.00–8.99 | High Prime (Moderately Abundant) |

With respect to the individual quality grade power spectrum 400, several factors can cause sound to reflect in soft tissue. The first is connective tissue which is different from muscle. It is a leaner material with a different protein. The second is fat, partly because of the connective tissue that it contains. When sound passes through a junction the change of speed, or impedance, will generate an ultrasonic return. This is because of measured reflection of the medium. A muscle with no fat and no connective tissue will generate a smooth return and generate few peaks because the muscle is uniform in makeup.

Thus, the presence of maxima and minima in a quality grade power spectrum are related to the amount of intramuscular fat, or marbling, contained in the meat. It has been determined that the number of local peaks in the FFT spectrum of a ultrasonic A Scan return signal signature generally corresponds to the percent of intramuscular fat in a sample of meat. That is, if the number of peaks in the FFT spectrum is 7, the meat contains approximately 7% fat and should be given the USDA quality classification of low prime.

Using the FFT, it can be seen that spectrum 400 of FIG. 8 produces five local maxima corresponding to five peaks 410, 420, 430, 440, 450. This suggests that a score of 5.00, and a USDA grade of average choice, is appropriate for the meat sample. To further refine the analysis, the number of lesser maxima can be taken into consideration as described below. Thus, the grade power spectrum of FIG. 8 has a lesser minima 435 and the score could be adjusted upward, perhaps to 5.50.

FIG. 8 represents only one of the three sample signatures taken around the twelfth and thirteenth rib area. An FFT is not required to be performed on the fourth (rumpfat) and fifth (backfat) signals.

Figure 9:
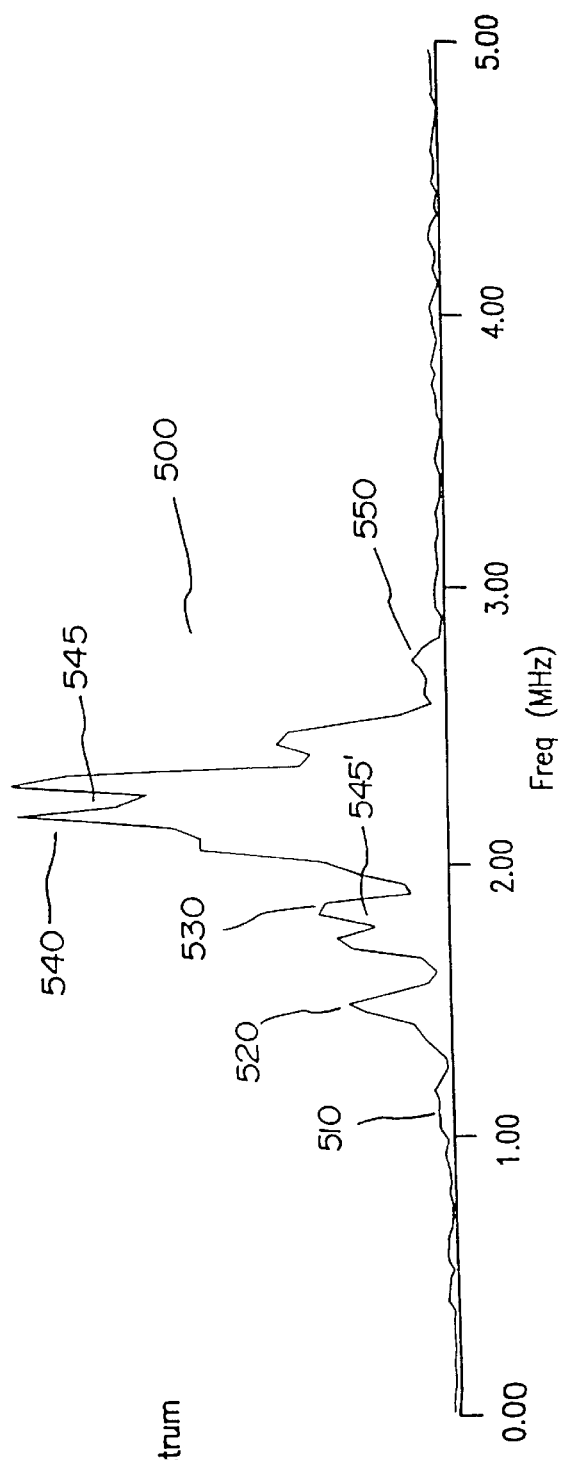
FIG. 9 shows a mean grade power spectrum for three signature samples.

To achieve a more accurate result, the grade spectrums of all three signatures should be combined. FIG. 9 shows such a mean grade power spectrum 500. The mean grade power spectrum 500 is generated using the three signatures obtained by placing the transducer at positions: above the twelfth rib; above the thirteenth rib; and between the twelfth and the thirteenth ribs. An individual grade power spectrum is generated for the grade sample gate area of each of the three signatures. The three individual grade power spectrums are combined to obtain the mean grade power spectrum 500. The mean grade power spectrum 500 can then be analyzed as described with respect to FIG. 8 to obtain a more accurate reading of intramuscular fat and, consequently, USDA quality grade for the meat. The five local maxima corresponding to the five peaks 510, 520, 530, 540, 550 and the minor minimas 545, 545' could represent a score of 5.50, and a USDA grade of average choice, for the meat represented by the spectrum shown in FIG. 9. This process is shown in FIG. 11 as steps 814, 816 and 818.

Figure 10:
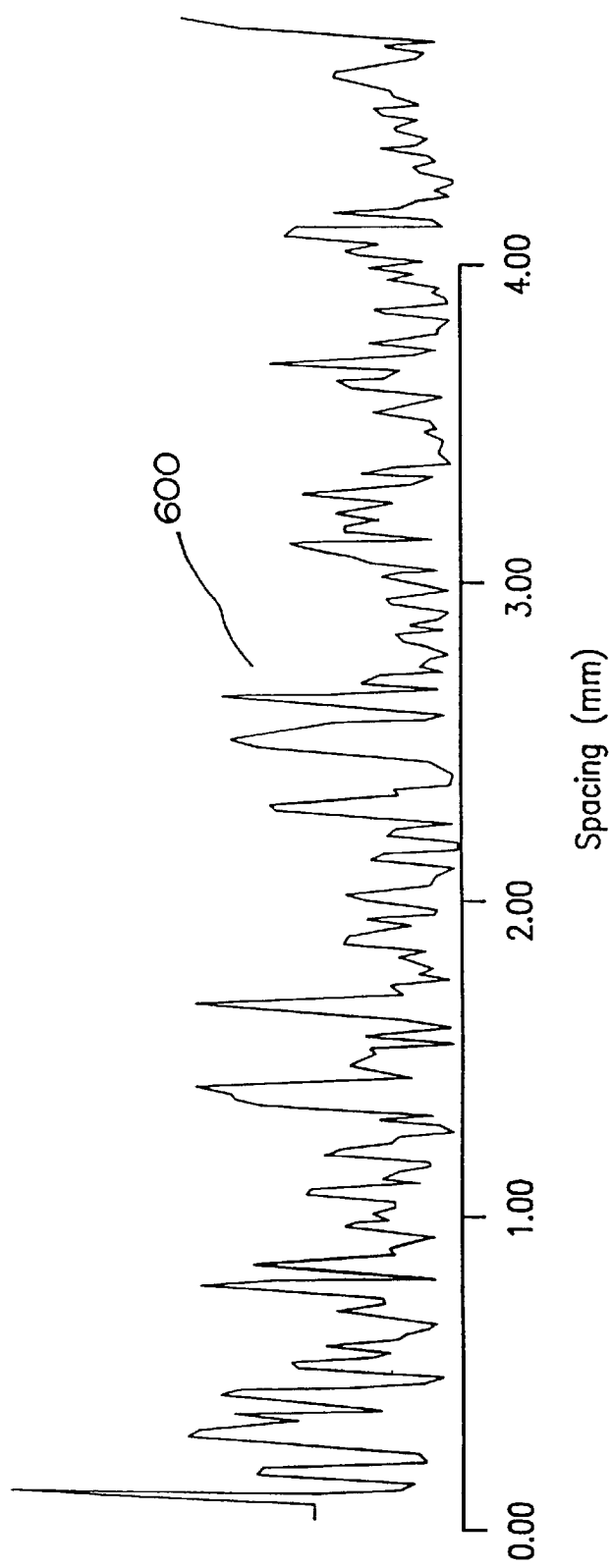
FIG. 10 shows a "merit" or tenderness chart of the mean grade power spectrum shown in FIG. 9.

FIG. 10 shows a merit number, or tenderness, chart of the mean grade power spectrum 500 shown in FIG. 9. The total energy loss of ultrasound as it moves through tissue is due to absorption, reflection and scattering. In addition to the fact that pure fat itself absorbs ultrasound, fat droplets in a tissue cause scattering. This elevated attenuation of ultrasound in fatty tissue is due to increased absorption and scattering of the ultrasound energy. This suggests that fat infiltration of tissue can be evaluated quantitatively and non-invasively. It has been determined that the granular structure of the tissue corresponds to the flavor and tenderness of the meat.

The merit number is computed by performing a cepstral analysis to obtain a wave form 600. The cepstrum is obtained by performing an FFT of the log-power spectrum. The spacing between peaks in the cepstrum is called spacing among scatters (SAS). While the first FFT performed on the return signature transformed a time domain signal into the frequency domain, the cepstral analysis transforms the frequency domain signal into the distance domain. It has been determined that the average of this wave form generally corresponds to the merit of the tissue sample. That is to say, given two pieces of meat with the same USDA quality grade, the meat with the lower average will generally be of a higher quality in terms of tenderness and flavor. This process is shown in FIG. 11 as steps 820 and 822.

Figure 12:
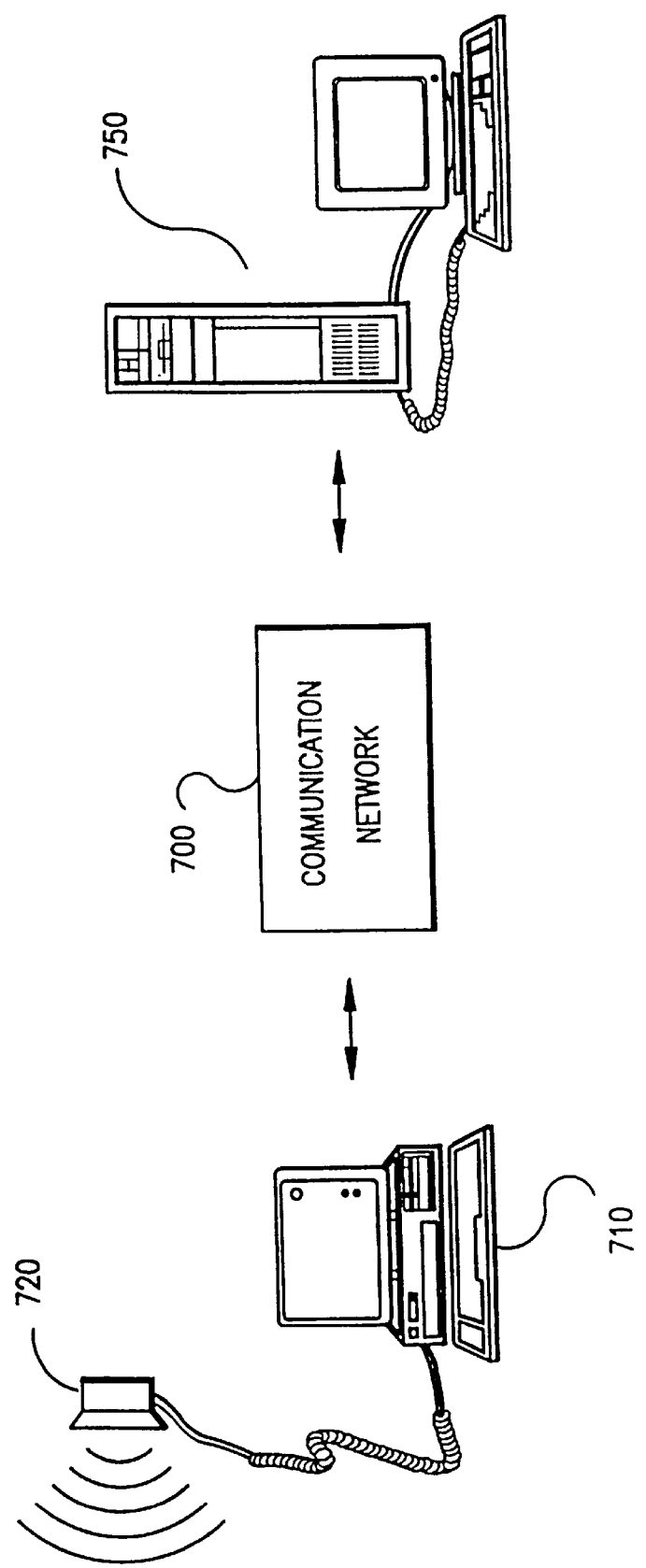
FIG. 12 shows the components of a measuring system according to a first embodiment of the present invention.

FIG. 12 shows the components of a measuring system according to a first embodiment of the present invention. A transducer 720 is connected to a first computer station 710 to record and digitize five signatures as described above for each sample of tissue. This data is transmitted through a communication network 700, such as the public telephone lines, the Internet or an Intranet to a second computer station 750. For example, the first computer station 710 could exchange data with the second computer station 750 via e-mail. The second computer station 750 analyzes the signatures as described with respect to FIGS. 6 through 10 to measure characteristics of the tissue. In the first embodiment of the present invention, the second computer station 750 is the server and the first computer station 710 is the client. Both computer stations 710, 750 can use the Microsoft Windows NT operating system version 4.0 or higher to handle telephone, Internet or Intranet communications. Using this configuration, many client computers 710 can be connected to a single server computer 750. The server computer 750 can verify the identity of a client computer 710 before processing the information. Moreover, the software used to analyze the ultrasonic return signatures only needs to be updated on the second computer 750 for improvements to the entire system.

FIG. 13 shows the components of a measuring system according to a second embodiment of the present invention. A transducer 720' is connected to a hand held general purpose ultrasonic detector/collector 730 (shown more particularly in FIG. 17), similar to the Krautkramer Branson DMS programmed with specialized measuring software. The hand-held detector/collector stores the digital signatures, which can be transferred to a first computer station 710' at a later time. As in the previous embodiment, this data is transmitted through a communication network 700' to a second computer station 750'. The second computer station 750' analyzes the signatures as described with respect to FIGS. 6 through 10 to measure characteristics of the tissue.

With either of the above embodiments, the second computer station 750, 750' can report the results of the measurements back to the first computer station 710, 710' through the communication network 700, 700' either on a sample-by-sample basis or in the form of a report containing a plurality of samples. Either the first computer station 710, 710' or the second computer station 750, 750' can use this information to create and maintain a database regarding a particular animal or a group of animals. The reports and database can be arranged based on the age of the animals, the quality of the meat, the date the signatures were taken, the genetic or family history of an animal, the owner of the animal, or any other identifying feature. These reports can then be used by the animal owners or feedlots to improve the quality of the herd.

In this way, the user can determine the quality grade and yield of a plurality of animals using the present invention. The user first measures the animals by placing the ultrasonic transducer at the four specified locations to obtain the five required signals. The fourth (rumpfat) and fifth (backfat) signals give the user an immediate determination of these quantities, which assists the user in identifying the characteristics of the animal. The other three signals must be combined and analyzed as discussed above. The present inventor envisions that process taking place at the second computer station 750, 750', but the first computer station 710, 710' or the hand held unit 730 may also be equipped to perform these calculations. The user may also send to the second computer 750, 750', via the communications network 700, the backfat and rumpfat measurements. Then, the second computer can calculate the body composition (also known as 'yield') based on these values. Thus, all the user need do is gather measurements for all his animals, and transmit the values to the second computer station for processing. He would then receive back from the second computer station a report indicating the quality grade and yield values for all measured animals. One important benefit of using a server computer, such as computers 750 and 750' above, is that the calculation software can be updated for all client computers, such as PCs 710 and 710', by updating the software at the server computer.

Since the measuring techniques of every user may be different, the attenuation characteristic shown in FIG. 6 will always vary. If this characteristic varies greatly from a 100% positive value, the quality of the measured signals will be poor. The second computer station 750, 750' can also be equipped to efficiently detect and compensate for the problems caused by inaccurate measurements.

Figure 15:
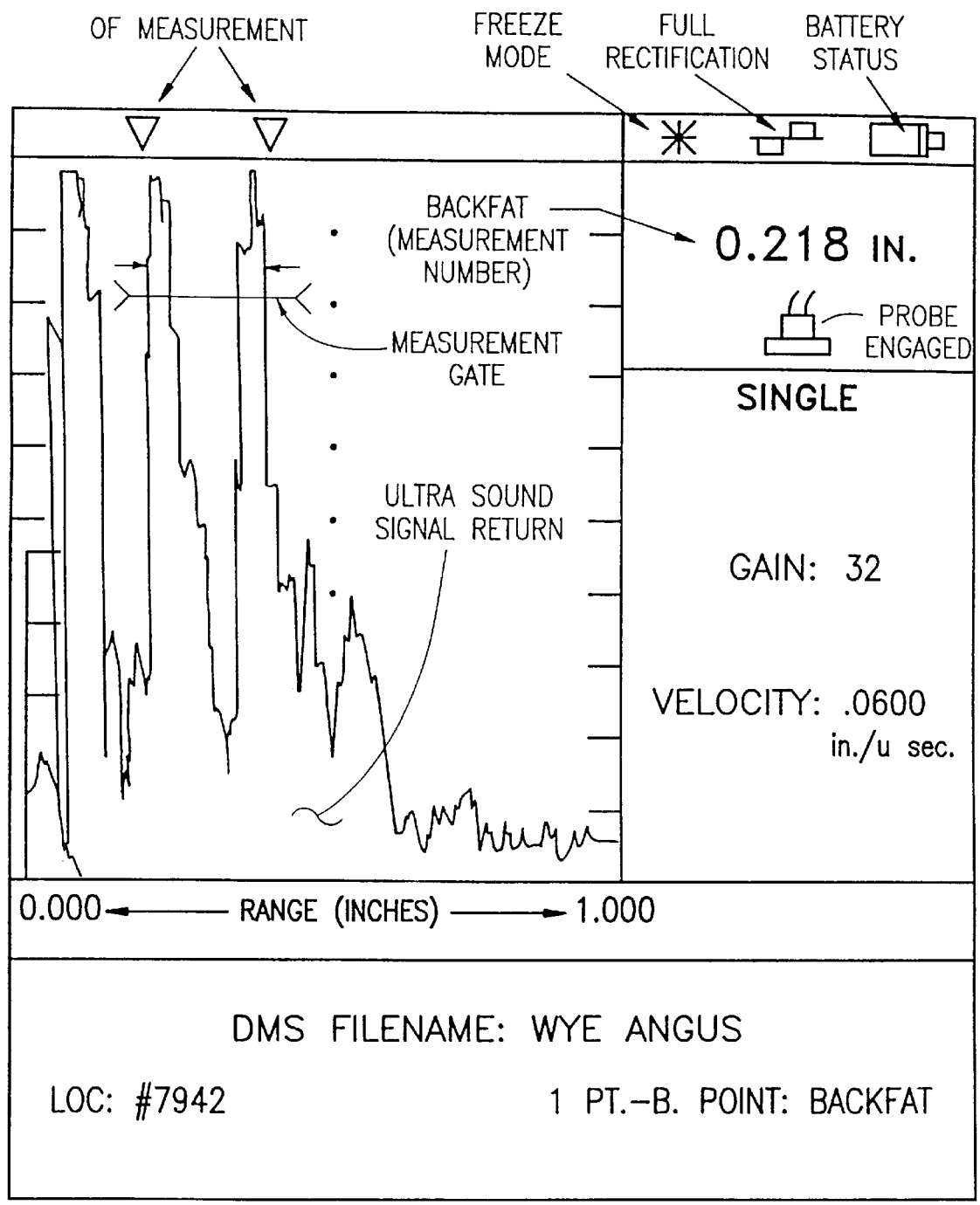
FIG. 15 shows a sample display of a hand-held unit which is measuring backfat according to a second embodiment of the present invention.
Figure 16:
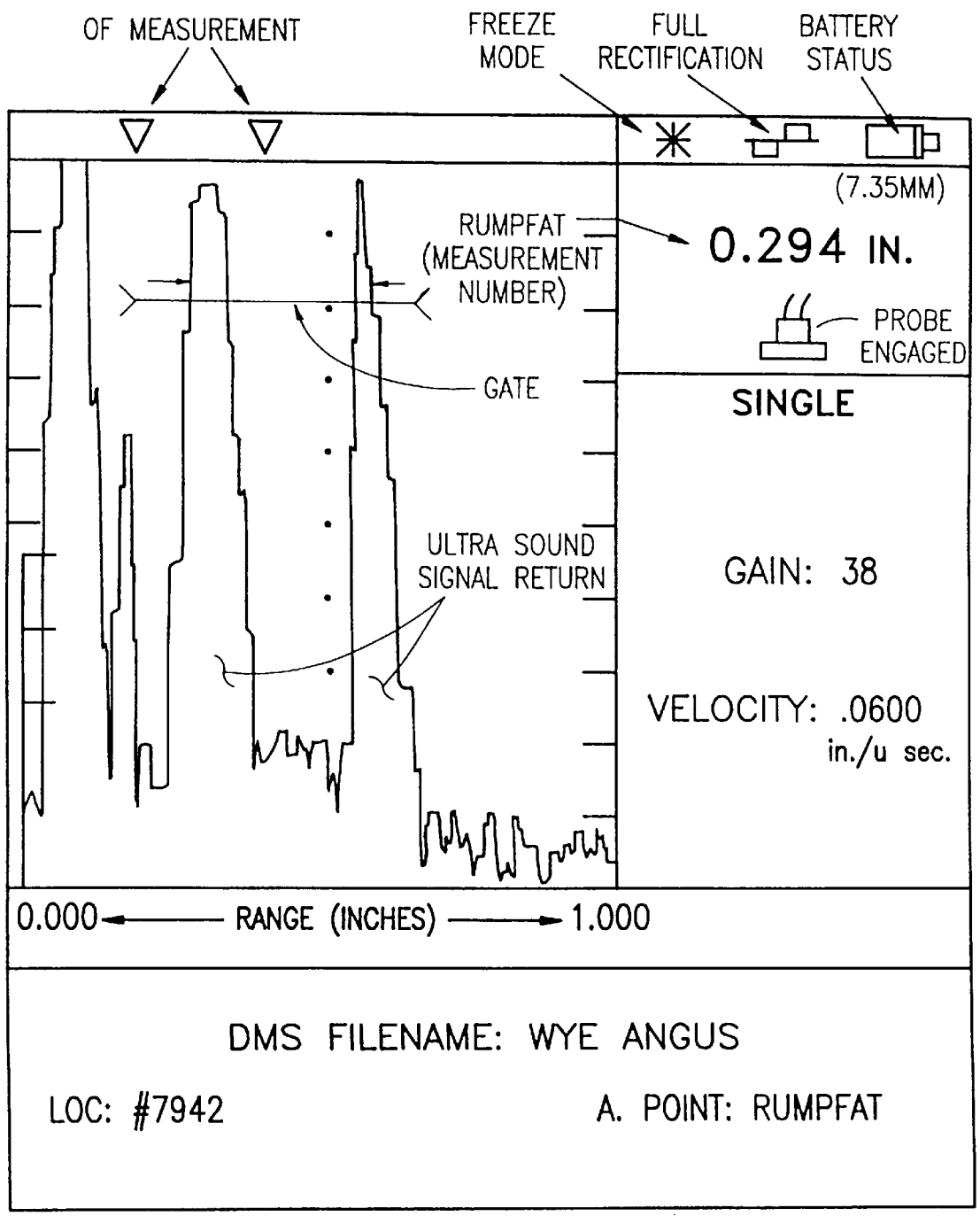
FIG. 16 shows a sample display of a hand-held unit which is measuring rumpfat according to a second embodiment of the present invention.

FIGS. 15 and 16 show examples of the screen displays which appear on the screen 736 of portable unit 730 shown in FIG. 17. FIG. 15 shows a measurement of backfat, while FIG. 16 shows a measurement of rumpfat. As can be seen from these figures, the portable unit 730 gives the user an instantaneous display of the depth of the rumpfat or backfat in inches or millimeters. The user can either utilize this information on his own, or he can send this information back to the second computer station 750, 750' (FIGS. 12 and 13) along with the other three measured signals to obtain yield and grade numbers for the entire animal. In either case, the measured values can be used to regulate the feeding parameters of the animals in order to keep the yield grade of the meat acceptable.

Figure 14:
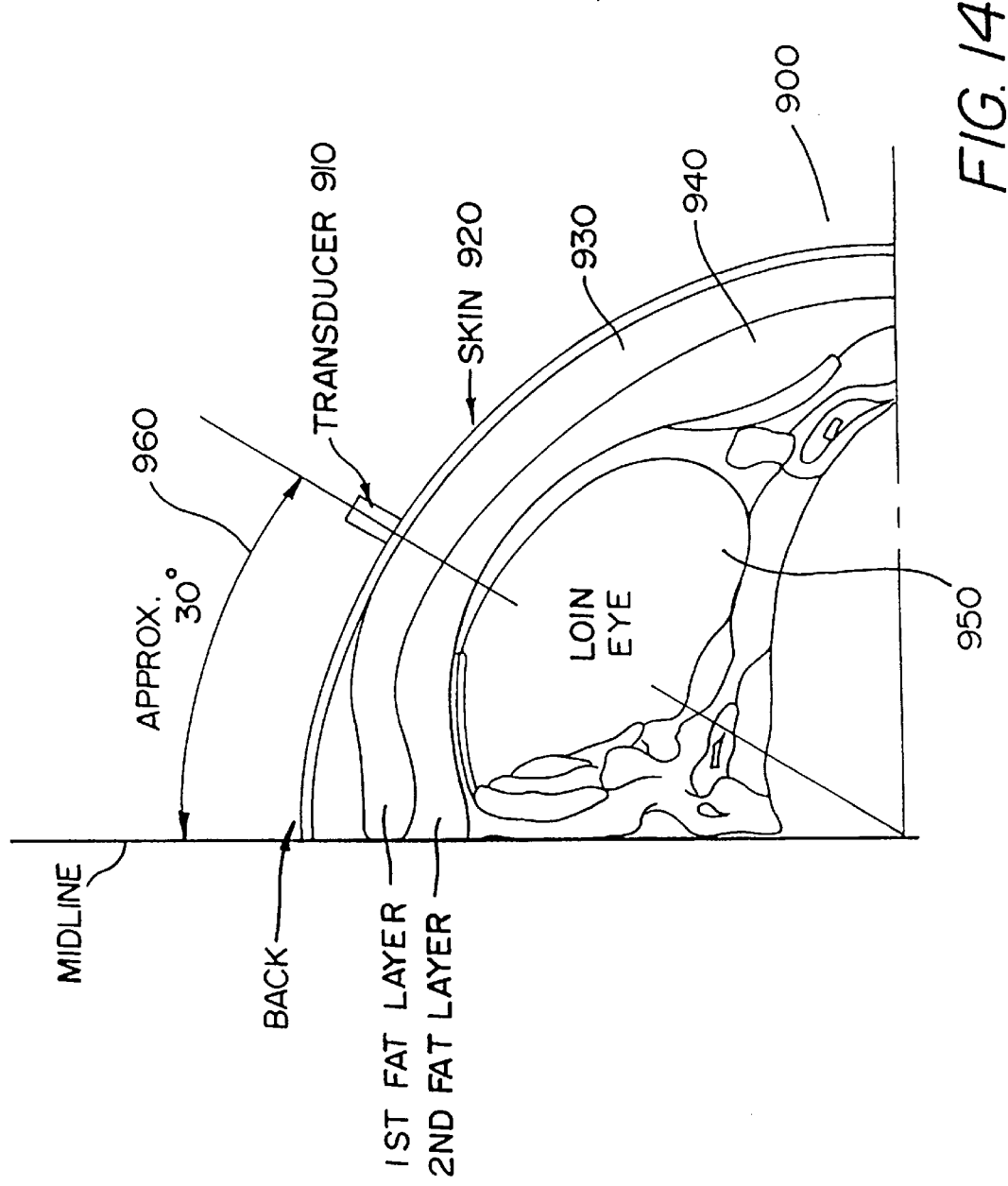
FIG. 14 shows a cross sectional skeletal view of a hog taken at the tenth rib.

While the above embodiments are directed to determining the characteristics of tissue on a beef animal, a similar approach could be used with hogs. FIG. 14 shows a cross sectional skeletal view of a hog 900 taken at the tenth rib. A transducer 910 can be placed on the hog's skin 920 at a predetermined angle 960. A process similar to that described with respect to FIGS. 3 through 11 can then be used to perform a quantitative analysis of ultrasonic A scan signals.

The sensitivity gain control curves stored in STC memory 162 may need to be customized to handle the ultrasonic return signals associated with hogs. Because the STC memory 162 can store multiple sensitivity gain control curves, it is possible that a single machine could store separate curves for beef animals and hogs. The operator could then chose the appropriate curve depending on the type of meat being examined.

Pork is assigned a quality grade in a manner similar to the grading of beef. Thus, a similar process can be used to determine the percentage of internal fat, the quality grade, and the merit number of the pork tissue. Moreover, as shown in FIG. 13, hogs have two layers of back fat 930, 940. The ultrasonic return signal can be analyzed to determine the depth of these back fat layers and the approximate size of a predetermined loin eye area 950. The ultrasonic A scan should be measured at the tenth rib, the last rib and in between the tenth and last rib.

Although preferred embodiments are specifically illustrated and described herein, it will be appreciated that modifications and variations can be made without departing from the teachings of the invention. Accordingly, the invention is not limited by the foregoing description, but is only limited by the scope of the appended claims.

What is claimed is:

1. An apparatus for measuring characteristics of at least one meat specimen, comprising:
    an ultrasonic transducer; and
    a portable hand-held computer connected to said ultrasonic transducer for transmitting A scan ultrasonic signals into a meat specimen and for receiving a plurality of return signals, said portable computer storing said plurality of received return signals, wherein said plurality of return signals are used to identify at least a merit number of the meat specimen.

2. An apparatus as in claim 1, further comprising:
    a second computer in communication with said portable computer, said second computer receiving said stored return signals for a meat specimen from said portable computer and determining characteristics of the meat specimen based on characteristics of said return signals.

3. An apparatus as in claim 2, further comprising:
    an electromagnetic radiation transmitter for transmitting said received return signals for a meat specimen from said portable computer to said second computer.

4. An apparatus for measuring characteristics of at least one meat specimen, comprising:
    an ultrasonic transducer;
    a portable hand-held computer connected to said ultrasonic transducer for transmitting A scan ultrasonic signals into a meat specimen and for receiving a plurality of return signals, said portable computer storing said plurality of received return signals wherein said plurality of return signals are used to identify at least a merit number of the meat specimen;
    a second computer in communication with said portable computer, said second computer receiving said stored return signals for a meat specimen from said portable computer and determining characteristics of the meat specimen based on characteristics of said return signals; and
    a third computer for receiving and storing said stored return signals for a meat specimen, said third computer transmitting said stored return signals to said second computer.

5. An apparatus as in claim 4 wherein said third computer communicates with said second computer through telephone lines.

6. An apparatus as in claim 4, wherein said third computer communicates with said second computer through the Internet.

7. An apparatus as in claim 4, wherein said third computer communicates with said second computer through a local area network.

8. An apparatus as in claim 1, wherein said portable computer determines a value representative of a backfat of the meat specimen from one of said stored return signals.

9. An apparatus as in claim 1, wherein said portable computer determines a value representative of a rumpfat of the meat specimen from one of said stored return signals.

10. An apparatus as in claim 2, wherein said second computer determines a value representative of a backfat of the meat specimen from one of said stored return signals.

11. An apparatus as in claim 2, wherein said second computer determines a value representative of a rumpfat of the meat specimen from one of said stored return signal.

12. An apparatus as in claim 1, wherein said portable computer stores at least five return signals for each meat specimen.

13. An apparatus as in claim 12, wherein said portable computer uses said five return signals to determine a quality grade and yield grade of said meat specimen.

14. An apparatus as in claim 2, wherein said portable computer stores at least five return signals for said meat specimen and said second computer uses said five return signals to determine a quality grade and yield grade of said meat specimen.

15. An apparatus as in claim 1, wherein said portable computer includes a display for displaying a representation of the ultrasonic return signals received by said ultrasonic transducer.

16. An apparatus as in claim 12, wherein said at least five signals include, at least three signals from the area near the twelfth and thirteenth ribs of the meat specimen, at least one signal indicative of a backfat of the meat specimen, and at least one signal indicative of a rumpfat of the meat specimen.

17. An apparatus as in claim 13, wherein said at least five signals include, at least three signals from the area near the twelfth and thirteenth ribs of the meat specimen, at least one signal indicative of a backfat of the meat specimen, and at least one signal indicative of a rumpfat of the meat specimen.

18. An apparatus as in claim 14, wherein said at least five signals include, at least three signals from the area near the twelfth and thirteenth ribs of the meat specimen, at least one signal indicative of a backfat of the meat specimen, and at least one signal indicative of a rumpfat of the meat specimen.

19. An apparatus as in claim 16, wherein said at least three signals from near the twelfth and thirteenth ribs of the meat specimen are used by the portable computer to determine a quality grade of the meat specimen.

20. An apparatus as in claim 17, wherein said at least three signals from near the twelfth and thirteenth ribs of the meat specimen are used by the portable computer to determine the quality grade of the meat specimen.

21. An apparatus as in claim 18, wherein said at least three signals from near the twelfth and thirteenth ribs of the meat specimen are used by the portable computer to determine the quality grade of the meat specimen.

22. An apparatus as in claim 16, wherein the at least one backfat signal and the at least one rumpfat signal are used by the portable computer to determine a yield grade of the meat specimen.

23. An apparatus as in claim 17, wherein the at least one backfat and the at least one rumpfat signal are used by the portable computer to determine the yield grade of the meat specimen.

24. An apparatus as in claim 18, wherein the at least one backfat signal and the at least one rumpfat signal are used by the portable computer to determine the yield grade of the meat specimen.

25. A method of measuring the characteristics of at least one meat specimen, comprising the steps of:
    transmitting ultrasonic signals into an animal using an A scan ultrasonic transducer connected to a portable hand-held computer;
    receiving a plurality of return signals using said A scan transducer; and
    determining the characteristics of the animal based on the characteristics of the return signals using the portable hand-held computer, wherein at least one of the characteristics of the animal is a merit number.

26. The method of claim 25, wherein at least three ultrasonic signals are transmitted into the animal, said at least three signals being used to determine a quality grade of the animal.

27. The method of claim 25, wherein at least two ultrasonic signals are transmitted into the animal, said signals being used to determine a yield grade of the animal.

28. The method of claim 25, wherein at least five signals are transmitted into the animal, at least two of said signals being used to determine a yield grade of the animal, and at least three of said signals being used to determine a quality grade of the animal.

29. The method of claim 26, wherein said at least three signals are transmitted into the animal in the area near the twelfth and thirteenth ribs.

30. The method of claim 27, wherein at least one of said at least two signals is transmitted into the animal in the area near the twelfth and thirteenth ribs.

31. The method of claim 27, wherein at least one of said at least two signals is transmitted into the animal in the rump area.

32. A method of measuring the characteristics of at least one meat specimen, comprising the steps of:
    transmitting ultrasonic signals into an animal using an A scan ultrasonic transducer;
    receiving at least one return of said ultrasonic signal using said A scan transducer; and
    determining at least a rumpfat and a merit number of the animal based on the characteristics of the at least one return signal.

33. A portable hand-held computer for measuring characteristics of a plurality of meat specimens, comprising:
    an ultrasonic transducer for transmitting A scan ultrasonic signals into one of said plurality of meat specimens and for receiving a plurality of return signals, said portable computer storing said plurality of return signals; and
    communication equipment for sending said plurality of return signals to a remote computer, wherein said plurality of return signals are used by said remote computer to identify at least a merit number of the meat specimen.

34. The portable hand-held computer according to claim 33, wherein at least one of said plurality of return signals is used to determine the rumpfat of one of the plurality of meat specimens.

35. The portable hand-held computer according to claim 33, wherein at least one of said plurality of return signals is used to determine a quality grade of one of the plurality of meat specimens.

36. The portable hand-held computer according to claim 33, wherein at least one of said plurality of return signals is used to determine the backfat of one of the plurality of meat specimens.

\* \* \* \* \*